United States Patent [19]

Zupancic et al.

[11] Patent Number: 4,664,761
[45] Date of Patent: May 12, 1987

[54] ELECTROCHEMICAL METHOD AND APPARATUS USING PROTON-CONDUCTING POLYMERS

[75] Inventors: Joseph J. Zupancic, Bensenville; Raymond J. Swedo, Mt. Prospect; Sandra L. Petty-Weeks, Naperville, all of Ill.

[73] Assignee: UOP Inc., Des Plaines, Ill.

[21] Appl. No.: 814,339

[22] Filed: Dec. 27, 1985

[51] Int. Cl.[4] .......................... C25B 1/02; H01M 8/10
[52] U.S. Cl. .................................. 204/129; 204/252; 204/277; 204/278; 429/30; 429/33; 429/192
[58] Field of Search .................... 429/30, 33, 192; 204/129, 130, 252, 277, 278, 421, 424, 425, 426, 427

[56] References Cited

U.S. PATENT DOCUMENTS 3,392,092 7/1968 Lawton et al. .................. 429/33 X
3,489,670 1/1970 Maget ............................. 204/129
4,295,952 10/1981 de Nora et al. ................ 204/252 X Primary Examiner—John F. Niebling
Assistant Examiner—Nam X. Nguyen
Attorney, Agent, or Firm—Thomas K. McBride; John F. Spears, Jr.; Richard J. Cordovano

[57] ABSTRACT

Apparatus and method for performing an electrochemical process involving hydrogen and gaseous compounds capable of dissociating into or combining with hydrogen ions using a solid electrolyte concentration cell. Specific applications are fuel cells for producing an electrical current and separation of hydrogen from a gaseous mixture. A novel proton-conducting membrane comprised of an interpenetrating polymer network serves as the solid electrolyte. For increased strength, a membrane may be composited with or utilized with a porous support.

20 Claims, 2 Drawing Figures

ELECTROCHEMICAL METHOD AND APPARATUS USING PROTON-CONDUCTING POLYMERS

FIELD OF THE INVENTION

This invention relates to an electrochemical process involving movement of protons through a membrane and applications thereof. More specifically, it relates to the use of a novel water-insoluble solid electrolyte and a catalyst in electrochemical processes such as producing electricity from hydrogen or gases capable of dissociating to yield hydrogen ions or in removing hydrogen from a gaseous mixture having a component capable of dissociating to yield hydrogen ions. The solid electrolyte is an interpenetrating polymer network.

BRIEF SUMMARY OF THE INVENTION

The present invention provides methods and apparatus for hydrogen separation and electricity production. A novel solid electrolyte membrane is used in the present invention. We have discovered that a water-insoluble membrane may be obtained by admixing sulfuric acid or a phosphoric acid with an organic polymer which is at least partially compatible with said acid to form a host polymer blend which, in combination with a guest polymer, forms an interpenetrating polymer network which is useful in electrochemical processes. This membrane is capable of acting as a proton conductor in a fuel cell or hydrogen separation system where a hydrogen compound yields protons on one side of the membrane, protons are transported through the membrane, and protons are combined with a substance on the other side.

In addition, the composition of matter utilized for said membrane may be composited on a flexible porous support to form a composite membrane which possesses increased strength as well as being a protonic conductor or it may be used with a rigid porous support. Examples of material used for such porous support include glass cloth, polysulfone, and ceramics. Even without a support, a membrane of the present invention is stronger than prior art membranes.

The invention utilizes a concentration cell whose electrolyte is said membrane or composite membrane. A membrane is mounted in a membrane housing having a first gas chamber and a second gas chamber, which chambers are separated by a partition comprising the membrane. Molecular transport through the membrane must be sufficiently slow so that gases will not mix by diffusing through it. Temperature of the gas or gases and/or the membrane housing may be controlled at a previously established value. A portion of catalytic agent for promotion of dissociation or combination is in intimate contact with the membrane on the membrane surface in common with the first gas chamber and also on the surface exposed to the second gas chamber. It is not necessary that the same catalytic agent be used on both sides. Means for forming electrical contact and transferring electrons to and from an external circuit are provided on each side of the electrolyte in intimate contact with catalytic agent. The catalytic agent may be platinum, palladium, or alloys thereof. The catalytic agent may be electrically conductive.

The method of a broad embodiment of the invention may be stated as a method for accomplishing an electrochemical process involving a gaseous mixture having a component which is capable, in the presence of a catalytic agent, of dissociating to yield hydrogen ions, such method comprising contacting said gaseous mixture with a first surface of an interpenetrating polymer network membrane and forming an electrical connection between two separate portions of catalytic agent effective to promote dissociation and combination, where a first portion of catalytic agent is in contact with said first surface and a second portion of catalytic agent is in contact with a second surface of said membrane, which membrane isolates said gaseous mixture from a second gas comprising hydrogen compounds formed at said second portion of catalyst, and which membrane has said second surface exposed to the second gas, said membrane comprising a host polymer blend and a guest polymer, where the host polymer blend is comprised of an acid selected from a group consisting of phosphoric acids and sulfuric acid and a polymer selected from a group of polymers or copolymers having repeat units selected from a group comprising hydroxyethylene, ethyleneimine, acrylic acid, ethylene oxide, 2-ethyl-2-oxazoline, polyphenolic structures such as phenol formaldehyde resins, acrylamide, N-substituted acrylamides, 4-vinylpyridine, methacrylic acid, N-vinylimidazole, vinyl sulfonic acid, and 2-vinylpyridine, and the guest polymer is formed from a monofunctional monomer selected from a group consisting of acrylic acid, methacrylic acid, acrylamide, methacrylamide, 2-acrylamido-2-methylpropanesulfonic acid, N-benzylacrylamide, N-ethylmethacrylamide, N-phenylacrylamide and N-phenylmethacrylamide, and a difunctional cross-linking agent selected from a group consisting of methylenebisacrylamide, N,N-diallylacrylamide, m-xylenebisacrylamide, and N,N'-trimethylenebisacrylamide.

It is among the objects of the present invention to provide an improved fuel cell utilizing a fuel gas comprising hydrogen or a gaseous component capable of dissociating into hydrogen ions. The first and second chambers of the membrane housing serve as a fuel gas chamber and an oxidant gas chamber. The fuel gas chamber contains a gas comprising hydrogen or a component capable of dissociating to form hydrogen ions. In the other chamber is an oxidant gas, such as a gas comprising oxygen, which combines with hydrogen ions which have passed through the membrane.

It is also among the objects of the present invention to provide methods and apparatus of separating hydrogen from a gaseous mixture containing hydrogen or a component capable of dissociating to yield hydrogen ions. Practice of the invention may be viewed as resulting in purification of the mixture by removal of hydrogen, purification of hydrogen, or addition of hydrogen to another gas. The first and second chambers of the membrane housing serve as a pure gas chamber and a mixture gas chamber. The term pure gas, as used herein, means hydrogen separated from the gas mixture along with whatever gas, if any, is in the pure gas chamber with the separated hydrogen.

BACKGROUND OF THE INVENTION

Figure 1:
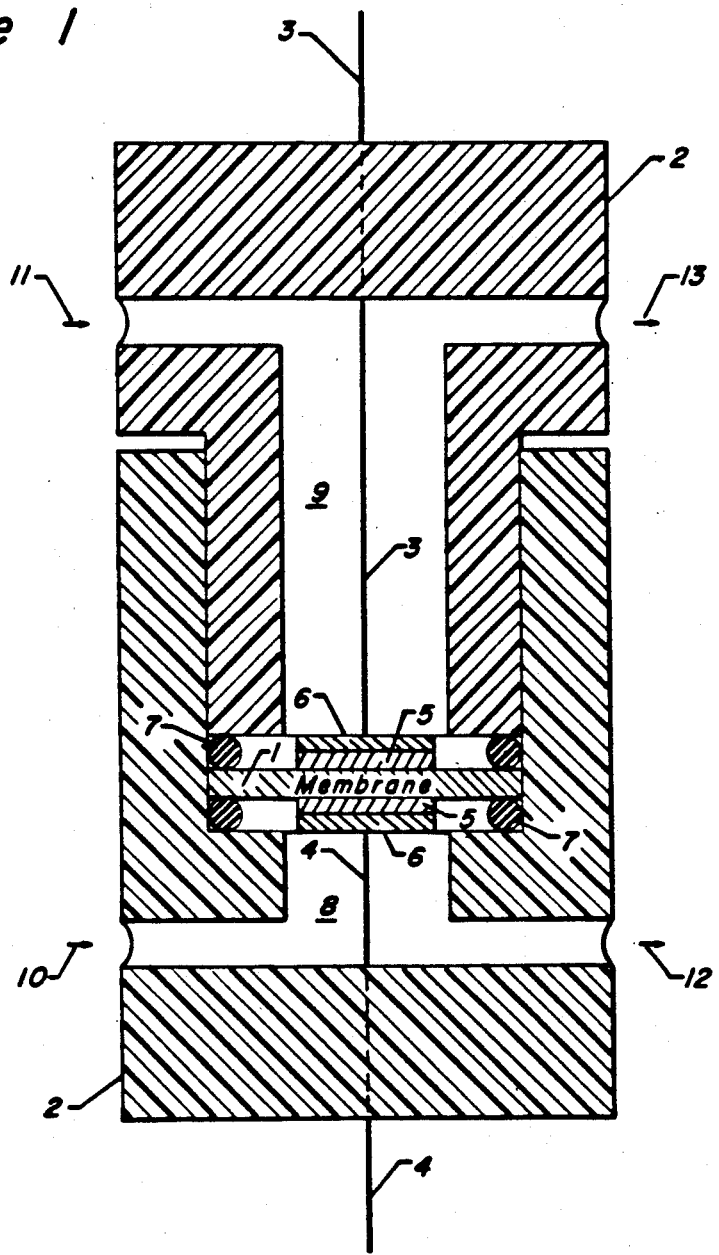
FIG. 1 is a schematic representation, in cross-section, of a test sensor used in initial proof of principle experimentation. The drawing is not to scale.

The present invention utilizes a solid electrolyte membrane in separation of hydrogen and production of electricity (a fuel cell). The Nernst equation describes the behaviour of such a system, as follows. When two media with different partial pressures, $P_1$ and $P_2$, of a particular substance present in both media are separated by a solid electrolyte (ionic conductor) and conducting electrodes are attached to both sides of the ionic conductor, an EMF is generated which is related to the partial pressures as follows:

$$EMF = E_o + \frac{RT}{nF} \ln \frac{P_2}{P_1},$$

where R is the gas constant, T is absolute temperature, F is the Faraday constant, $E_o$ is the standard oxidation-reduction potential difference, EMF is electromotive force, and n is the number of electrons per molecule of product from the overall cell reaction.

If the system described by the above equation behaves nonideally, the partial pressures must be replaced by fugacities. Another factor which may need to be considered in regard to a particular system is the rate of dissociation to form the ions which pass through the solid electrolyte. This may be a limiting factor to the transfer of ions through the electrolyte. The rate of dissociation can be calculated by means of the equilibrium constant for the dissociation reaction.

In a majority of cases, the admixture of an organic compound, especially in a polymeric state, with an inorganic compound, results in a phase separation, due to the fact that the two systems are immiscible in nature. However, a macroscopically homogeneous polymer blend, which we term a host polymer blend, may be prepared by admixing organic and inorganic components as discussed herein; the resulting substance (the host polymer blend) is not merely a physical mixture but exhibits a degree of interaction, that is, some amount of chemical interaction exists. The host polymer blend is then admixed with a monomer and a difunctional cross-linking agent in a compatible solvent. The mixture is cast on a smooth surface and the solvent removed to form a membrane. The monomer is polymerized to form a polymer termed the guest polymer, thereby forming an interpenetrating polymer network membrane.

Interpenetrating polymer networks are known to those skilled in the art. There are three general classes of interpenetrating polymer networks: sequential, simultaneous, and latex. The classes differ in method of preparation. In order to prepare an interpenetrating polymer network of the sequential class, a first polymer, termed a host polymer, is prepared in the absence of a second monomer. The host polymer is then mixed with a second monomer and a cross-linking agent in a compatible solvent. After removal of the solvent, the second monomer and cross-linking agent are polymerized to yield the guest polymer of the interpenetrating polymer network and the guest polymer is cross-linked to itself. An interpenetrating polymer network is more than a blend of two polymers. It is a new polymer system having properties which are a combination of those possessed by the host polymer and the guest polymer. However, there is no chemical bonding between the host and guest polymers. In the new polymer system, the host and guest polymer chains are permanently entangled, or intertwined, with one another. It is impossible to separate the two polymers by chemical methods (such as leaching or dissolving one polymer away from the other). It can be seen that the present invention may be termed an interpenetrating polymer network.

Substances which are permeable by gases in a selective manner are known and utilized in a variety of applications. A membrane formed in accordance with the present disclosure is substantially impermeable to ions and gases, including hydrogen gas, but does allow hydrogen ions to pass through it. It should be noted that the membrane is not expected to be totally impermeable and that substances in addition to hydrogen ion may pass through it. Permeability experimentation has not been done, except to the extent indicated herein. For background information relating to the principles of the present invention, reference may be made to the book *Solid Electrolytes and Their Applications,* edited by Subbarao, Plenum Press, 1980.

Low mechanical strength has been a common problem when attempting to apply permselective membranes. The present invention provides a membrane whose mechanical strength is increased by compositing it with other materials, but whose desirable properties are not lost as a result of doing so.

In a simple hydrogen-oxygen fuel cell, the fuel gas is hydrogen and the oxidant gas is oxygen. Hydrogen dissociates into hydrogen ions and electrons at the catalyst on the fuel gas side of the membrane. The hydrogen ions pass through the electrolyte element while the electrons flow through the external circuit, doing electrical work before forming water by combining with, at the catalytic agent on the oxidant gas side of the membrane, hydrogen ions which passed through the membrane and oxygen. A flow of gases is normally maintained for continuous operation of the fuel cell. The maximum voltage which can be produced by a fuel cell is a thermodynamic function of the fuel and oxidant. For a hydrogen-oxygen fuel cell, the theoretical EMF is 1.23 volts. The actual voltage will be less due to losses within the cell. The current produced is controlled by such considerations as the rate at which the electrochemical reactions proceed, the electrolyte thickness, and the catalyst surface area. In a simple hydrogen-oxygen cell, the partial pressure term of the Nernst equation partial pressure of water divided by the quantity partial pressure of hydrogen times square root of partial pressure of oxygen.

When producing hydrogen by means of the electrochemical process of this invention, the amount produced is generally in accordance with the parameters discussed above: the Nernst equation and, where applicable, the dissociation equilibrium constant. The rate at which separation takes place may be increased by adding means to generate an EMF to the external circuit. That is, a difference in partial pressures is sufficient to provide the driving force for hydrogen ion transport through the membrane, but applying an externally generated driving force will increase hydrogen ion flux. In the practice of all embodiments of this invention, it should be noted that exact adherence to theoretical relationships is not required of commercially used methods and apparatus.

DETAILED DESCRIPTION OF THE INVENTION

As was mentioned above, in attempting to blend an organic polymer with an inorganic compound, the usual result is to obtain a phase separation. It has now been discovered that a useful substance may be obtained by means of the methods described herein. The resulting composition of matter is formed into a thin film membrane which may be utilized in electrochemical systems such as gas separation processes and electric power production. The utility of these membranes in electrochemical systems is due to the fact that the membranes possess a high protonic conductivity, especially at room or ambient temperature, and are resistant to water.

Usually, high conductivity is observed in polymer complexes only when the temperature is above the glass transition temperature (Tg), that is, above the temperature at which the substance changes from a glassy state to a rubbery state (the melting point of a polymer is usually above its glass transition temperature). Indications of the change of a polymer from a glassy state to a rubbery state are abrupt changes in certain properties, such as coefficient of expansion and heat capacity. The compositions of the present invention exhibit high protonic conductivity at temperatures well below the observed glass transition temperatures of the individual homopolymers. A device utilizing an ion-conducting polymer must operate below the Tg of the polymer; the polymer is not usable at higher temperatures due to loss of strength, tackiness, etc.

A distinct advantage which is possessed by the polymer-blend membranes of the present invention over other organic-inorganic blend membranes is that these membranes possess low resistivities (resistance times area divided by thickness).

The host polymer blend is a blend of an organic polymer and a phosphoric acid or sulfuric acid, the polymer being at least partially compatible with the acid. Examples of organic polymers which may be employed as one component of the host polymer blend of the present invention will include poly(vinyl alcohol), also known as PVA, polyethyleneimine, poly(acrylic acid), polyethylene oxide, phenol formaldehyde resins, poly(vinylpyrrolidone), poly(ethyloxazoline), poly(acrylamide), poly(vinylimidazole), poly(vinylpyridine), poly(vinyl sulfonic acid), etc. Further examples of organic polymers which may be employed include copolymers having monomer units of these exemplary polymers. In terms of monomer repeat units, the polymer-blend membrane comprises a polymer selected from a group of polymers or copolymers having repeat units selected from a group comprising hydroxyethylene, ethyleneimine, acrylic acid, ethylene oxide, 2-ethyl-2-oxazoline, acrylamide, N-substituted acrylamides, 4-vinylpyridine, methacrylic acid, N-vinylimidazole, vinyl sulfonic acid, 2-vinylpyridine, and polyphenolic structures such as phenol formaldehyde resins.

Examples of acids which may be employed in the host polymer blend will include hypophosphoric acid, metaphosphoric acid, orthophosphoric acid, pyrophosphoric acid, polyphosphoric acid, or sulfuric acid. The sulfuric acid which is employed will comprise an aqueous sulfonic acid which may contain from about 10% to about 40% sulfuric acid in aqueous solution. It is to be understood that the aforementioned organic polymers and phosphoric acids or sulfuric acid are only representative of the class of components which make up the membrane blends used in the present invention.

The guest polymer is formed from a monofunctional monomer selected from a group comprised of acrylic acid, methacrylic acid, acrylamide, methacrylamide, 2-acrylamido-2-methylpropanesulfonic acid, N-benzylacrylamide, N-ethylmethacrylamide, N-phenylacrylamide, and N-phenylmethacrylamide. The monofunctional monomer which is employed to form the guest polymer differs from any of the monomeric repeat units which comprise the organic polymer in the host polymer blend so that an interpenetrating polymer network may be formed.

Examples of difunctional cross-linking agents for the guest polymer are methylenebisacrylamide, N,N-diallylacrylamide, m-xylenebisacrylamide, and N,N'-trimethylenebisacrylamide.

The host polymer blend used in the present invention is prepared by admixing the two components of the blend in a mutually miscible solvent at solution conditions for a period of time sufficient to form the desired blend. In the preferred host polymer blend the mutually miscible solvent which is employed to dissolve the components comprises water, although it is contemplated within the scope of this application that any other mutually miscible solvent, either inorganic or organic in nature may also be employed. The mixing of the two components of the host polymer may be effected at solution conditions which will include a temperature in the range of from about ambient (20°–25° C.) up to the boiling point of the mutually miscible solvent which, for example, in the case of water is 100° C. As an example, poly(vinyl alcohol) and orthophosphoric acid may be placed in a flask and dissolved in water which has been heated to 100° C.

The monofunctional monomer and cross-linking agent are then mixed with PVA and acid at a temperature ranging from ambient to about 50° C. The blend is cast upon a suitable casting surface which may consist of any suitable material sufficiently smooth in nature so as to provide a surface free of any defects which may cause imperfections on the surface of the membrane. Examples of suitable casting surfaces may include metals such as stainless steel, aluminum, etc., glass, polymer or ceramics. After casting the solution upon the surface, the solvent is then removed by any conventional means including natural evaporation or forced evaporation by the application of elevated temperatures whereby said solvent is evaporated and the desired membrane comprising a thin film is formed. Evaporation may be effected at room temperature over a period of time ranging up to about 24 hours or may be effected by subjecting the film to elevated temperatures up to about 40° C. for a shorter time. Evaporation may also be effected by subjecting the solution to reduced pressure as low as 10 mm Hg at ambient or elevated temperatures. The thickness of the film can be controlled by the amount of phosphoric or sulfuric acid and/or polymer which is present in the reaction mixture or by the depth of the casting vessel. The thin film membrane which is prepared according to the process of the present invention will possess a thickness which may range from about 0.1 to over 500 microns and preferably from about 20 to about 100 microns.

After evaporation of the solvent, the resulting membrane is cured, or cross-linked, by various methods well known in the art. For example, the membrane may be subjected to radiation from an ultraviolet source or from an electron beam. Another method of curing, or polymerizing, the monomer is to subject the membrane to elevated temperatures ranging from about 50° to about 80° C. in an inert atmosphere, such as nitrogen, and in the presence of an activator, such as azoisobutyronitrile (AIBN). Curing is the final step in forming the membrane of this invention.

The amounts of phosphoric or sulfuric acid and organic polymer used in the host polymer blend may vary over a relatively wide range. For example, the acid may be present in the lend in a range of from about 16 mol% to about 50 mol% of the host polymer blend while the organic polymer may be present in an amount in the range of from about 84 mol% to about 50 mol% of the host polymer blend. Whenever a composition is expressed herein, it is to be understood that it is based, in the case of polymers, on the monomer repeat unit.

The mole ratio of monomer to cross-linking agent may vary from 35 moles of monomer to 1 mole of agent to 1 mole of monomer to 10 moles of agent. The mole ratio of host polymer blend to guest polymer may range from 5:1 to about 1:20.

It will be helpful in gaining an understanding of the invention to examine initial proof of principle experimentation. The information presented in regard to this experimentation is not meant to limit the scope of the invention in any way. This experimentation was directed to obtaining information on gas detection, as well as the specific applications described above.

EXAMPLE 1

A solution was prepared by dissolving 0.5 gram of poly(vinyl alcohol) and 0.2 ml of 85% by weight orthophosphoric acid in boiling deionized water, the amount of water being sufficient to yield a total volume of 25 ml. The molecular weight of the PVA was 133,000. Other commercially available molecular weights could have been used. A second solution was prepared by mixing 2 grams of methylenebisacrylamide, 30.1 grams of methacrylic acid, and 25 grams of water. Portions of the two solutions in the amount of 6.7 ml and 10 ml respectively were mixed together and poured into a Petri dish, which served as a casting vessel. The water was allowed to evaporate for a period of 24 hours. The resulting film was transparent and possessed a thickness of 110 microns. The membrane was then irradiated by using an electron beam at a power of 175 kiloelectron volts (KEV) and a dose of 5 megarads (Mrad)/pass. It was irradiated on one side.

A thin film membrane was cut into a disc having a 1" diameter to form membrane 1 of FIG. 1 ad platinum was sputter-deposited onto both sides of the disc. The deposited platinum discs each had a thickness of about 400 Angstroms and a diameter of about 1 cm. Deposition was accomplished by means of a Hummer II sputter deposition system supplied by Technics Co. A biased screen between the target and film was used to reduce the electron flux to the membrane. There are many alternative methods which could have been used to form the platinum deposits, such as thermal evaporation or deposition by means of an ink. The porous structure of sputter-deposited catalytic agent is helpful in facilitating spillover of hydrogen ions onto the membrane, but it is not required. Note that hydrogen will migrate through solid platinum.

Referring to FIG. 1, membrane 1 was mounted in test fixture 2, which may also be referred to as a sample cell, membrane housing, or test sensor. The above mentioned platinum deposits 5 served as catalytic agent to promote dissociation and reassociation or combination. Electrical contact was made to the platinum through copper platens 6, which were held in place by springs (not shown) extending between the platens and interior surfaces of the sample cell. Platens 6 did not cover the entire surface of the catalytic agent, though FIG. 1 shows this to be the case. Note that when the catalytic agent is electrically conductive and not discontinuous, electrical contact need be made only at one point, the catalytic agent thus serving as an electrode. Wire leads 3 and 4 extended from the platens out of the test fixture through means for sealing against gas leakage (not shown). Leads 3 and 4 were connected to EMF and current detection means (not shown). Membrane 1 was sealed into test fixture 2 by O-rings 7 so that there were no gas leakage paths between first gas chamber 8 and second gas chamber 9. In a fuel cell embodiment, these chambers are denoted fuel gas chamber and oxidant gas chamber, while in a hydrogen separation embodiment, they are called pure gas chamber and mixture gas chamber. Tubing (not shown) was connected at the gas inlets as denoted by arrows 10 and 11 to provide gas flow into chambers 8 and 9 and was also connected to the gas outlets as denoted by arrows 12 and 13 to conduct gas away from the chambers. Gas cylinders and gas mixing and flow control apparatus (not shown) were used to provide gas for testing in accordance with the herein described experiments. Several cylinders of hydrogen/nitrogen gas mixtures were purchased; an analysis of the contents was supplied with each cylinder.

Gas flows were established through the chambers of the sample cell with both chamber pressures at about one atmosphere, since the chambers were vented directly to atmosphere. One flow was pure hydrogen (hydrogen partial pressure of approximately 1.0 atm.) and the other was alternated between pure hydrogen and about a 10% by volume mixture of hydrogen in nitrogen (hydrogen partial pressure of approximately 0.1 atm.). The voltage across wires 3 and 4 was recorded by means of a standard laboratory strip chart recorder. The voltage versus time plot was a substantially perfect square wave form. Voltage varied consistently between 0.1 millivolts and 29.2 mv. Response was Nernstian; the calculated voltage is approximately 29.1 mv (at a room temperature of about 22° C.). Note that this is open circuit voltage.

When an ammeter was connected to wires 3 and 4, the measured current was about $2 \times 10^{-3}$ ma. This corresponds to a current density of about $1.3 \times 10^{-3}$ ma/cm$^2$ and a hydrogen flux of $1.8 \times 10^{-5}$ ft$^3$/ft$^2$-hr; both figures being based on the area of the membrane covered by platinum. EMF across the membrane was measured when 100% hydrogen was flowing through both chambers of the sample cell. From this a resistivity of $2 \times 10^6$ ohm-cm was calculated. This applies to a totally dry membrane. When a membrane which had dried for only 1 hour, as mentioned above, was placed under test, the initial resistance was lower. The increase in resistance is due to removal of the water used in the casting process during initial operation of a sensor.

EXAMPLE 2

A test fixture was prepared and tested in the same manner as that of EXAMPLE 1, except that both sides of the membrane were irradiated instead of one side as in EXAMPLE 1. The measured voltages were 0 mv and 29.0 mv. Resistivity was $6.9 \times 10^5$ ohm-cm. Hydrogen flux was $5 \times 10^{-5}$ ft$^3$/ft$^2$-hr.

EXAMPLES 3, 4 AND 5

A test fixture was prepared and tested in the same manner as that of EXAMPLE 1, except that the amounts of the components was varied as shown below. All amounts are in grams.

|  | Example 3 | Example 4 | Example 5 |
|---|---|---|---|
| PVA | 0.50 | 0.50 | 0.50 |
| orthophosphoric acid | 0.29 | 0.56 | 0.56 |
| methacrylic acid | 2.69 | 0.54 | 2.69 |
| methylenebisacrylamide | 0.18 | 0.04 | 0.18 |

The EMF difference (Delta EMF) in mv, resistivity in $10^5$ ohm-cm, and calculated hydrogen flux (F) in ft$^3$/ft$^2$-hr after at least 24 hours under test were as follows:

|  | Delta EMF | R | F |
|---|---|---|---|
| Example 3 | 28.9 | 51 | $6.2 \times 10^{-6}$ |
| Example 4 | 29.3 | 1.9 | $1.9 \times 10^{-4}$ |
| Example 5 | 29.4 | 2.3 | $1.3 \times 10^{-4}$ |

Water solubility was tested by placing membranes made in accordance with the above examples in boiling water. Also placed in boiling water was a membrane cast from a solution of PVA and orthophosphoric acid in a 3.8 to 1 mole ratio (Example 6). The two component membrane dissolved in about 90 seconds while the interpenetrating polymer network membranes were unaffected after 15 minutes in boiling water.

In addition to platinum, palladium may be deposited on membranes for use as catalytic agent. Other catalytic agents are available and known to those skilled in the art. The catalytic agent need not be electrically conductive; however, then the means for forming electrical connection must be in contact with the catalytic agent over a broad area, to faciliate movement of electrons from sites of the catalytic agent to the electrically conductive substance, or electrode. Areas of membrane which are not adjacent to catalytic agent are not effective in the invention. Hydrogen ions spill over from the catalytic agent to the membrane and then the protons move through the membrane.

It is believed that membranes of the present invention will operate at temperatures ranging from minus 30° C. to plus 50° C. and will exhibit Nernstian behavior, though, of course, the voltage varies with temperature. It may be possible to use these membranes at higher temperatures, but no tests have been conducted.

It can be seen that a membrane mounted in a cell such as depicted in FIGS. 1 and 4 may be subjected to high differential pressures which may deform or burst the membrane. A composite membrane or supported membrane assembly may be used when a high differential pressure across the membrane is expected. A composite membrane may be fabricated by casting a solution prepared as described above on a flexible porous support and then curing it. A supported membrane assembly may be fabricated by attaching a membrane which is cast, dried, and cured as above to a rigid porous support. A supported membrane may also be fabricated by impregnating a rigid porous support with solid electrolyte, allowing it to dry, casting a membrane on the support and allowing it to dry, and then casting another membrane on the reverse side, thus forming a continuous solid electrolyte path from the outer surface of the membrane on one side through the electrolyte to the outer surface of the membrane on the other side of the support. It is contemplated that any porous substrate which possesses a structural strength greater than the thin film membrane may be employed. Some examples of these porous supports will include substances such as glass cloth, polysulfone, cellulose acetate, polyamides, ceramics such as alumina, glass, porcelain, etc. which have been fabricated to possess the necessary porosity, etc. The amount of blend which is cast upon the flexible porous support will be that which is sufficient to form a thin film membrane having a thickness within the range herein set forth.

Composite membranes using the composition of matter of the present invention have not been tested, though supported membranes of the present invention have been tested. However, it is expected that present composited membranes will exhibit behavior at least as good as the tested composited membranes. In one test, a polymer blend was prepared by dissolving 0.5 gram of 16,000 molecular weight poly(vinyl alcohol) and 0.2 ml of orthophosphoric acid in boiling deionized water, the amount of organic polymer and acid being sufficient to impart a 63/37 wt. % ratio to the resulting polymer blend. After a period of time sufficient to form the blend had passed, the solution was stirred and poured onto the top of a fine glass cloth which was positioned in a standard Petri dish. The water was allowed to evaporate for a period of 48 hours and the resulting membrane composite comprising a thin film membrane composited on, or with, the glass cloth having a thickness of 95 microns was recovered.

The PVA/H$_3$PO$_4$ composite membrane was cut into a circle having a 1" diameter and platinum electrodes were sputter-deposited on each side of the membrane. The membrane was then placed in a sample housing similar to that of FIG. 1. A reference gas consisting of 100% hydrogen and a sample gas comprising 90.013% nitrogen and 9.987% hydrogen were each passed through the two chambers. An EMF of 29.6 mv was measured; this compares to a calculated voltage of 29.5 millivolts at a temperature of 25.3° C. In addition, it was found that the resistivity was $0.375 \times 10^5$ ohm-cm.

As an illustration of the greater structural strength of a polymer blend on a porous flexible support when compared to unsupported membranes reference may be made to previous experiments. In previous experiments, two polymer blend membranes were prepared. The polymer blend was prepared by dissolving 0.5 gram of poly(vinyl alcohol) having a molecular weight of 16,000 and 0.2 ml of orthophosphoric acid in boiling deionized water. The resulting blend was cast onto a glass cloth having a thickness of 30 microns. A second blend was prepared by admixing like proportions of poly(vinyl alcohol) and orthophosphoric acid and casting the resulting blend onto a Petri dish without a support. After removal of the solvent, the two membranes were recovered.

Each membrane was placed in a holder which enabled air pressure to be exerted against one side of the membrane while the other side was at atmospheric pressure. When exposed to 5 psig, the unsupported membrane burst at its center in less than 1 minute. At 2 psig another sample of unsupported membrane bulged and was permanently deformed. The composite membrane was subjected to various pressure levels in 5 psig increments with one minute hold time between increases in pressure. In burst at 35 psig, shearing at the edges of the test hole in the holder. The point of failure leads one to believe that holder design caused the shearing and that a higher burst pressure would be observed in a different holder.

In an experiment using the composition of matter of the present invention, a supported hydrogen sensor was made by impregnating a porous ceramic support with a water solution containing 2 grams PVA, 2.2 grams orthophosphoric acid, 5.39 grams methacrylic acid, 0.36 grams methylenebisacrylamide, and 0.06 grams AIBN. A Coors porous ceramic substrate measuring 1½ inch diameter and ⅛ inch thick was soaked in the solution and allowed to dry. Additional solution was applied to each side of the impregnated substrate and allowed to dry. The sensor was heated in nitrogen for 2 hours at 75° C. The formation of the interpenetrating polymer network was confirmed after two hours by placing a film of the above composition made at the same time in boiling water for 15 minutes. The film did not dissolve. Platinum electrodes were sputter-deposited on each side of the sensor as described previously. The sensor detects hydrogen and has a total device resistance in 100% hydrogen of 1.07 megohm. When a differential of 100 psig was established across this supported sensor, there was no damage to the sensor.

The membranes of the present invention are quite strong and durable, as can be seen from values obtained for the bulk modules. The membrane of Example 6 consisted of a blend of PVA and phosphoric acid in a 3.8:1 mole ratio. Examples 3 and 5 were interpenetrating polymer networks where the host polymer blend was PVA and orthophosphoric acid in 3.8:1 and 2:1 mole ratios, respectively. In the following table, the bulk modulus was measured at 25° and 50° C. and is expressed in meganewtons per square meter.

|  | Modulus @ 25 | Modulus @ 50 |
| --- | --- | --- |
| Example 6 | 85 | 65 |
| Example 3 | 1093 | 503 |
| Example 5 | 237 | 217 |

Any substance capable of dissociating in the presence of a catalyst to yield hydrogen ions may be the subject of separation in the same manner as is elemental hydrogen. The Nernst equation is applicable; the $E_o$ term is not 0, as it is when the same substance is present on both sides of the membrane, and the partial pressure term of the equation contains the partial pressures of the substances of the reaction, raised to the proper power if more than one molecule of a substance is involved. As examples, certain hydrocarbons come readily to mind as substances which may be hydrogenated or dehydrogenated, these hydrocarbons including cyclopentadiene, 1,3-pentadiene, isoprene, benzene, 2-butene-1,4-diol, n-hexane, cyclohexane, and isoamylene.

In the embodiment of the invention depicted in FIG. 1, when test fixture 2 is used for gas separation, it is necessary that lead 3 be connected to lead 4 by an electrical conduction path. This path permits the electrons resulting from the dissociation of hydrogen (or other gaseous mixture component) at one catalyst portion 5 to travel to the other side of the membrane to combine at the other catalyst portion with hydrogen ions which have passed through the membrane. If means for generating an EMF are inserted into the electrical conduction path, that is, if electrical power from a source external to the separation apparatus is supplied to the apparatus through the means for forming electrical connection such as leads 3 and 4, the rate of removal of hydrogen from the gaseous mixture will increase.

For a practical separation process, the partial pressure of hydrogen in the chamber from which hydrogen is removed, the mixture gas chamber, must be higher than the partial pressure of hydrogen in the chamber in which hydrogen collects after removal, the pure gas chamber. In an industrial application of the invention, a compressor might be used to compress the gaseous mixture from which hydrogen is to be removed, maintaining the hydrogen partial pressure in the mixture gas chamber higher than that in the pure gas chamber. The partial pressure of hydrogen increases as the total pressure is increased. The pure gas chamber might be subjected to a negative pressure, or vacuum, thus removing hydrogen as it collects, or forms. The references to hydrogen partial pressure deal with a case in which hydrogen is the gaseous mixture component which dissociates to form hydrogen ions. If the component is not hydrogen, the equilibrium hydrogen partial pressure associated with the gaseous mixture component must be at a higher value than the partial pressure of hydrogen in the pure gas chamber, where the product gas comprising hydrogen is collected.

It should be noted that the Nernst equation contains a temperature term. Since temperature is a factor in the separation it may be desirable to change the temperature of the gases before the electrochemical reaction takes place.

Figure 2:
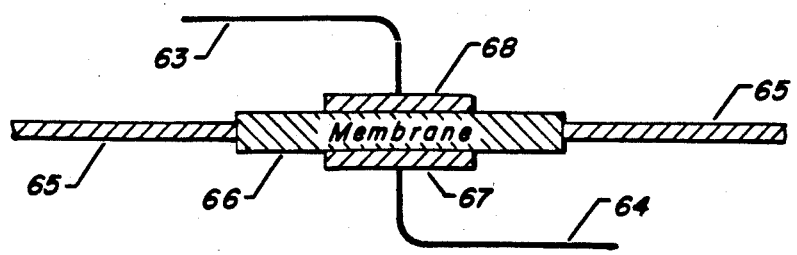
FIG. 2 depicts an embodiment of the invention, in a sectional view, in which a membrane is part of a partition separating a fuel gas chamber from an oxidant gas chamber or a pure gas chamber from a mixture gas chamber.

Referring to FIG. 2, an embodiment of the invention in which a membrane 66 serves as part of partition 65 is shown. Partition 65 separates a mixture gas chamber from a pure gas chamber. Catalytic agents 67 and 68 and wire leads 63 and 64 perform the functions discussed above. Leads 63 and 64 must be connected to one another. Separation apparatus may take many forms; FIG. 2 shows a simple and basic form. A cascade arrangement might be used, in which the gaseous mixture is compressed and then allowed to flow through a plurality of mixture chambers, each at a lower pressure.

The design of fuel cells is well known. Many configurations are possible; FIG. 1 provides an example of one type. FIG. 2 depicts an embodiment of the present invention useful in producing electricity as well as in separation. Partition 65 separates a fuel gas chamber from an oxidant gas chamber. Electrically conductive catalytic agent is present on both sides of membrane 66, as shown by reference numbers 67 and 68. Wire leads 63 and 64 extend to connect to electricity utilizing means (not shown).

Sample cell or membrane housing or test fixture refers to a housing or fixture which holds an electrolyte element and other required components. FIG. 1 depicts a membrane housing. Membrane or electrolyte element refers to an ion-conducting substance suitable for use as an electrolyte in the concentration cell of this invention which has been formed into a particular physical entity, either with or without additional substances, for use in the invention. Where an electrolyte element surface is referred to as in common with a gas or gas chamber, the meaning is the same as exposed to a gas or gas chamber and such reference does not preclude the presence of catalytic agent and electrodes at or covering the surface. Gas may diffuse through covering material. Gas chamber refers to any space in which gas which is the subject of this electrochemical process exists. The term "gas" is used herein to include vaporized liquids regardless of boiling point characteristics of the substance. As used herein, miscible means capable of being mixed where there may only be a very small degree of solubility. As is familiar to those skilled in the art, the terms concentration and partial pressure are often used interchangeably; partial pressure expresses concentration. A gaseous mixture may be formed in the apparatus by the dissociation of hydrogen when a single compound is charged to the apparatus, such as in the dehydrogenation of a hydrocarbon. A fuel gas may have only one component or more than one. Compatible may be taken to mean that compatible compounds will form the polymer-blend composition of matter.

We claim as our invention:

1. Apparatus for the separation of hydrogen from a gaseous mixture having a component which is capable, in the presence of a catalytic agent, of dissociating to yield hydrogen ions, comprising
   (a) an interpenetrating polymer network membrane which comprises a host polymer blend and a guest polymer, wherein the host polymer blend is comprised of (1) an acid selected from the group consisting of phosphoric acids and sulfuric acid and (2) a component selected from the group consisting of (i) a polymer selected from the group consisting of poly(hydroxyethylene), poly(ethyleneimine), poly(acrylic acid), poly(ethylene oxide), poly(2-ethyl-2-oxazoline), phenol formaldehyde resins, poly(acrylamide), poly(N-substituted acrylamide), poly(4-vinylpyridine), poly(methacrylic acid), poly(N-vinylimidazole), poly(vinyl sulfonic acid), and poly(2-vinylpyridine) and (ii) copolymers having monomer units of (i); and wherein the guest polymer is comprised of (1) a monofunctional monomer selected from the group consisting of acrylic acid, methacrylic acid, acrylamide, methacrylamide, 2-acrylamido-2-methylpropanesulfonic acid, N-benzylacrylamide, N-ethylmethacrylamide, N-phenylacrylamide and N-phenylmethacrylamide and (2) a difunctional cross-linking agent selected from the group consisting of methylenebisacrylamide, N,N-diallylacrylamide, m-xylenebisacrylamide and N,N'-trimethylenebisacrylamide, with the proviso that the monofunctional monomer which is employed to form the guest polymer differs from any of the monomeric repeat units which comprise the organic polymer in the host polymer blend;
   (b) a membrane housing comprising a first gas chamber and a second gas chamber separated by a partition comprising said membrane, said membrane having a first surface in common with the first gas chamber and a second opposing surface in common with the second gas chamber;
   (c) two portions of catalytic agent effective to promote dissociation and combination associated with each particle, one portion in contact with said first surface of said membrane and one portion in contact with said second opposing surface of said membrane; and
   (d) means to supply a gaseous mixture containing hydrogen to said first gas chamber.

2. The method of claim 1 further characterized in that said component is elemental hydrogen.

3. The apparatus as set forth in claim 1 in which said phosphoric acid is present in said host polymer blend in an amount in the range of from about 16 mol% to about 50 mol% and said polymer is present in said host polymer blend from about 50 mol% to about 84 mol%.

4. The apparatus as set forth in claim 1 in which said monofunctional monomer and said difunctional cross-linking agent are present in quantities such that the mole ratio of said monomer to said cross-linking agent varies from about 35:1 to about 1:10.

5. The apparatus as set forth in claim 1 in which said membrane possesses a thickness of from about 0.1 to about 500 microns.

6. The apparatus as set forth in claim 1 in which the mole ratio of said host polymer blend to said guest polymer is from about 5:1 to about 1:20.

7. The apparatus as set forth in claim 1 in which said host polymer blend comprises poly(vinyl alcohol) and orthophosphoric acid.

8. The apparatus of claim 1 further characterized in that said monofunctional monomer is methacrylic acid and said cross-linking agent is methylenebisacrylamide.

9. The apparatus as set forth in claim 1 in which said interpenetrating polymer network membrane is composited with a flexible porous support comprising glass cloth.

10. The apparatus as set forth in claim 1 in which said interpenetrating polymer network membrane is utilized with a rigid porous support.

11. The apparatus of claim 1 further characterized in that said catalytic agent comprises a metal selected from a group consisting of platinum, palladium, and alloys thereof.

12. The apparatus of claim 1 further characterized in that said catalytic agent is electrically conductive.

13. The apparatus of claim 1 further characterized in that said catalytic agent is porous to said gaseous component.

14. The apparatus of claim 1 further comprising means to adjust the operating temperature of said gaseous mixture.

15. The apparatus of claim 1 further comprising means to supply said gaseous mixture to one of said gas chambers and to remove gas comprising hydrogen from the other of said gas chambers.

16. A method for the separation of hydrogen from a gaseous mixture having a component which is capable, in the presence of a catalytic agent, of dissociating to yield hydrogen ions, said method comprising
   (a) providing an interpenetrating polymer network membrane which comprises a host polymer blend and a guest polymer, wherein the host polymer blend is comprised of (1) an acid selected from the group consisting of phosphoric acids and sulfuric acid and (2) a component selected from the group consisting of (i) a polymer selected from the group consisting of poly(hydroxyethylene), poly(ethyleneimine), poly(acrylic acid), poly(ethylene oxide), poly(2-ethyl-2-oxazoline), phenol formaldehyde resins, poly(acrylamide), poly(N-substituted acrylamide), poly(4-vinylpyridine), poly(methacrylic acid), poly(N-vinylimidazole), poly(vinyl sulfonic acid), and poly(2-vinylpyridine) and (ii) copolymers having monomer units of (i); and wherein the guest polymer is comprised of (1) a monofunctional monomer selected from the group consisting of acrylic acid, methacrylic acid, acrylamide, methacrylamide, 2-acrylamido-2-methylpropanesulfonic acid, N-benzylacrylamide, N-ethylmethacrylamide, N-phenylacrylamide and N-phenylmethacrylamide and (2) a difunctional cross-linking agent selected from the group consisting of methylenebisacrylamide, N,N-diallylacrylamide, m-xylenebisacrylamide and N,N'-trimethylenebisacrylamide, with the proviso that the monofunctional monomer which is employed to form the guest polymer differs from any of the monomeric repeat units which comprise the organic polymer in the host polymer blend, with two portions of catalytic agent effective to promote dissociation and combination being associated with the membrane, one portion in contact with said first surface of said membrane and one portion in contact with said second surface of said membrane; and (b) contacting said first surface of said membrane with said gaseous mixture while recovering hydrogen formed at said second surface.

17. An apparatus for producing electricity from a fuel gas having as a gaseous component which is capable, in the presence of a catalytic agent, of dissociating to yield hydrogen ions comprising:

(a) a polymer-blend membrane which comprises an interpenetrating polymer network membrane which comprises a host polymer blend and a guest polymer, wherein the host polymer blend is comprised of (1) an acid selected from the group consisting of phosphoric acids and sulfuric acid and (2) a component selected from the group consisting of (i) a polymer selected from the group consisting of poly(hydroxyethylene), poly(ethyleneimine), poly(acrylic acid), poly(ethylene oxide), poly(2-ethyl-2-oxazoline), phenol formaldehyde resins, poly(acrylamide), poly(N-substituted acrylamide), poly(4-vinylpyridine), poly(methacrylic acid), poly(N-vinylimidazole), poly(vinyl sulfonic acid), and poly(2-vinylpyridine) and (ii) copolymers having monomer units of (i); and wherein the guest polymer is comprised of (1) a monofunctional monomer selected from the group consisting of acrylic acid, methacrylic acid, acrylamide, methacrylamide, 2-acrylamido-2-methylpropanesulfonic acid, N-benzylacrylamide, N-ethylmethacrylamide, N-phenylacrylamide and N-phenylmethacrylamide and (2) a difunctional cross-linking agent selected from the group consisting of methylenebisacrylamide, N,N-diallylacrylamide, m-xylenesbisacrylamide and N,N'-trimethylenebisacrylamide, with the proviso that the monofunctional monomer which is employed to form the guest polymer differs from any of the monomeric repeat units which comprise the organic polymer in the host polymer blend;

(b) a membrane housing comprising a first fuel gas chamber and a second oxidant gas chamber separated by a partition comprising said membrane, said membrane having a first surface in common with the first fuel gas chamber and a second opposing surface in common with the second oxidant gas chamber;

(c) two separate portions of catalytic agent effective to promote dissociation and combination, a first portion in contact with said first surface of said membrane and a second portion in contact with said second surface of said membrane;

(d) means for forming electrical connection in operative contact with said catalytic agent at said first surface and with said catalytic agent at said second surface;

(e) means to supply fuel gas to said fuel gas chamber; and (f) means to supply oxidant gas to said oxidant gas chamber.

18. The apparatus of claim 17 further comprising means to utilize electricity connected between said means for forming electrical connection.

19. The apparatus of claim 17 further comprising means for maintaining equilibrium hydrogen partial pressure associated with the fuel gas at a value higher than the equilibrium hydrogen partial pressure in the gas chamber containing oxidant gas.

20. A method for accomplishing an electrochemical process using a gaseous mixture having a gaseous component which is capable, in the presence of a catalytic agent, of dissociating to yield hydrogen ions, such method comprising the steps of (a) providing a polymer-blend membrane which comprises an interpenetrating polymer network membrane which comprises a host polymer blend and a guest polymer, wherein the host polymer blend is comprised of (1) an acid selected from the group consisting of phosphoric acids and sulfuric acid and (2) a component selected from the group consisting of (i) a polymer selected from the group consisting of poly(hydroxyethylene), poly(ethyleneimine), poly(acrylic acid), poly(ethylene oxide), poly(2-ethyl-2-oxazoline), phenol formaldehyde resins, poly(acrylamide), poly(N-substituted acrylamide), poly(4-vinylpyridine), poly(methacrylic acid), poly(N-vinylimidazole), poly(vinyl sulfonic acid), and poly(2-vinylpyridine) and (ii) copolymers having monomer units of (i); and wherein the guest polymer is comprised of (1) a monofunctional monomer selected from the group consisting of acrylic acid, methacrylic acid, acrylamide, methacrylamide, 2-acrylamido-2-methylpropanesulfonic acid, N-benzylacrylamide, N-ethylmethacrylamide, N-phenylacrylamide and N-phenylmethacrylamide and (2) a difunctional cross-linking agent selected from the group consisting of methylenebisacrylamide, N,N-diallylacrylamide, m-xylenebisacrylamide and N,N'-trimethylenebisacrylamide, with the proviso that the monofunctional monomer which is employed to form the guest polymer differs from any of the monomeric repeat units which comprise the organic polymer in the host polymer blend, with two portions of catalytic agent effective to promote dissociation and combination being associated with the membrane, one portion in contact with said first surface of said membrane and one portion in contact with said second surface of said membrane;

(b) forming an electrical connection between said separate portions of catalytic agent; and (c) contacting said first surface of said membrane with said gaseous mixture while isolating said gaseous mixture from a second gas comprising hydrogen compounds formed at said second surface during said contacting step.

* * * * *